(12) United States Patent
Raivio et al.

(10) Patent No.: US 6,291,194 B1
(45) Date of Patent: Sep. 18, 2001

(54) ASSAY FOR DETERMINATION OF ANDROGENIC OR ANTI-ANDROGENIC ACTIVITY OF A SERUM SAMPLE OR A TEST COMPOUND

(76) Inventors: Taneli Raivio, Kalevanvainio 4 as 2, FIN-02100 Espoo; Jorma J. Palvimo, Lumikintie 7 D 37, FIN-00820 Helsinki; Olli A. Jänne, Hiiralankaari 23 B 12, FIN-02160, Espoo, all of (FI)

( * ) Notice: Subject to any disclaimer, the term of this patent is extended or adjusted under 35 U.S.C. 154(b) by 0 days.

(21) Appl. No.: 09/628,277

(22) Filed: Jul. 28, 2000

(51) Int. Cl.$^7$ .............................. G01N 33/53; C12Q 1/66

(52) U.S. Cl. ................................. 435/7.1; 435/7.8; 435/8

(58) Field of Search .............................................. 435/6, 8

(56) References Cited

U.S. PATENT DOCUMENTS 5,789,170 * 8/1998 Chang et al. ........................... 435/6

OTHER PUBLICATIONS

David J. Mangelsdorf, et al., "The Nuclear Receptor Superfamily: The Second Decade", Dec. 15, 1995, Cell vol. 83, 835–839.
Elizabeth Langley, et al., "Evidence for an Anti–parallel Orientation of the Ligand–activated Human Androgen Receptor Dimer", Dec. 15, 1995, Journal Biological Chemistry vol. 270, pp. 29983–29990.
Tarja Ikonen, et al., Interaction between the Amino–and Carboxyl–terminal Regions of the Rat Androgen Receptor Modulates Transcriptional Activity and Is Influnced by Nuclear Receptor Coactivators, Nov. 21, 1997, Journal Biological Chemistry vol. 272, pp. 29821–29828.
Jon A. Kemppainen, et al., "Distinguishing Androgen Receptor Agonists and Antagonists: Distinct Mechanisms of Activation by Medroxyprogesterone Acetate and Dihydrotestosterone", 1999, Molecular Endocrinology vol. 13 No. 3 pp. 440–454.
Anu–Maarit Moilanen, et al., "A Testis–specific Androgen Receptor Coregulator That Belongs to a Novel Family of Nuclear Proteins", Feb. 5, 1999, Journal Biological Chemistry vol. 274 No. 6, pp. 3700–3704.
A. Moilanen, et al., "The presence of a transcription activation function in the hormone–binding domain of androgen receptor is revealed by studies in yeast cells", Jun. 6, 1997, FEBS Letters vol. 412 pp. 355–358.
Ralph I. Dorfman, "Androgens and Anabolic Agents", 1962, Chapter 6 pp. 275–313, Method in Hormone Research, vol. II. New York, Academic Press.

* cited by examiner

Primary Examiner—Kenneth R. Horlick
Assistant Examiner—Teresa Strzelecka
(74) Attorney, Agent, or Firm—Rothwell, Figg, Ernst & Manbeck, P.C.

(57) ABSTRACT

The present invention is directed to methods for determining the androgenic or anti-androgenic activity of a sample and to a cell useful in these methods. To determine androgenic activity, the sample is contacted and incubated with a cell comprising i) a luciferase reporter plasmid,
  ii) a fusion protein comprising a ligand-binding domain of the androgen receptor and a Gal4 DNA-binding domain, said fusion protein being able to bind to binding sites in said luciferase reporter plasmid,
  iii) a fusion protein comprising an N-terminal region of the androgen receptor and a transcriptional activation domain, and
  iv) an androgen receptor-interacting protein 3.

The cell is then lysed and the luciferase activity of the lysate is measured. The measured luciferase activity is compared to that obtained by repeating the above method except that a control is added instead of the sample, to give the relative luciferase activity of the sample. The relative luciferase activity is used to detect or quantify an active androgen in the sample.

13 Claims, 4 Drawing Sheets

Without androgen

With androgen

Activation of luciferase gene expression

Without androgen

With androgen

ASSAY FOR DETERMINATION OF ANDROGENIC OR ANTI-ANDROGENIC ACTIVITY OF A SERUM SAMPLE OR A TEST COMPOUND

FIELD OF THE INVENTION

This invention relates to methods for determining androgenic or anti-androgenic activity of a sample, wherein the sample is either mammalian serum or a solution of a compound to be tested. The invention further concerns a cell useful in said methods.

BACKGROUND OF THE INVENTION

The publications and other materials used herein to illuminate the background of the invention, and in particular, cases to provide additional details respecting the practice, are incorporated by reference.

Androgens are required for the masculinization of male genitalia in utero, the development of secondary sex characteristics in boys, and the maintenance of male sexual function in adult life. After entering the target cell, androgens bind to androgen receptor (AR)—a ligand-dependent transcription factor. After binding of the hormone, AR enters the nucleus and binds to the regulatory region of the target gene as a homodimer. AR belongs to the nuclear receptor superfamily comprising receptors for various forms of vitamin $D_3$, thyroid hormones, retinoids, and steroid hormones (1). These receptors have conserved DNA—and ligand-binding domains (DBD and LBD, respectively), and variable hinge and N-terminal regions (1). In the case of AR, the N-terminal region encompasses the primary transcriptional activation domain. Upon androgen binding, LBD and the N-terminal region of AR have been shown to interact, which is suggested to facilitate AR dimerization (2,3), modulate transcriptional activity (4), and stabilize the receptor at low ligand concentrations (5).

AR-interacting protein 3 (ARIP3), a 572-amino acid nuclear protein expressed primarily in the testis, represents a potential coregulator of AR-dependent transcription (6). Although the exact physiologic role of ARIP3 is not yet known, we have observed that it can considerably facilitate the androgen-dependent interaction between the AR LBD and N-terminal region (6). Herein, we report the development of a bioassay that is based on ARIP3-facilitated interaction between the LBD and N-terminal region of AR. This assay appeared useful for quantitation of circulating androgen bioactivity in pediatric patients. We expect that the assay will have wide ramifications in clinical endocrinology.

SUMMARY OF THE INVENTION

Thus, according to one aspect this invention concerns a method for determining the androgenic activity of a sample, comprising the steps of a) contacting the sample with a cell comprising
   a luciferase reporter plasmid,
   a fusion protein comprising a ligand-binding domain of the androgen receptor and a Gal4 DNA-binding domain, said fusion protein being able to bind to binding sites in said luciferase reporter plasmid,
   a fusion protein comprising an N-terminal region of the androgen receptor and a transcriptional activation domain, and
   an androgen receptor-interacting protein 3,
b) allowing the sample to incubate with said cell,
c) lysing said cell,
d) measuring the luciferase activity of the lysate,
e) comparing the measured luciferase activity to that obtained by repeating the steps a) to d) above except that a control is added instead of the sample, to give the relative luciferase activity of the sample, and
f) using the relative luciferase activity to detect or quantify an active androgen in the sample.

According to another aspect, the invention concerns a method for determining the anti-androgenic activity of a compound, comprising the steps of
a) measuring the luciferase activity emitted from a first sample comprising a first compound having androgenic activity as described above,
b) measuring the luciferase activity, according to the previous step, emitted from a second sample comprising said first compound having androgenic activity and either I) a second compound which shall be tested in respect of anti-androgenic activity, or II) mammalian serum,
c) comparing the luciferase activities obtained in steps a) and b) above, and
d) using a decreased luciferase activity emitted from said second sample to detect or quantify the anti-androgenic activity of said second compound or serum.

According to a third aspect, the invention concerns a cell comprising
   a luciferase reporter plasmid,
   a fusion protein comprising a ligand-binding domain of the androgen receptor and a Gal4 DNA-binding domain, said fusion protein being able to bind to binding sites in said luciferase reporter plasmid,
   a fusion protein comprising an N-terminal region of the androgen receptor and a transcriptional activation domain, and
   an androgen receptor-interacting protein 3.

DETAILED DESCRIPTION OF THE INVENTION

Figure 1A:
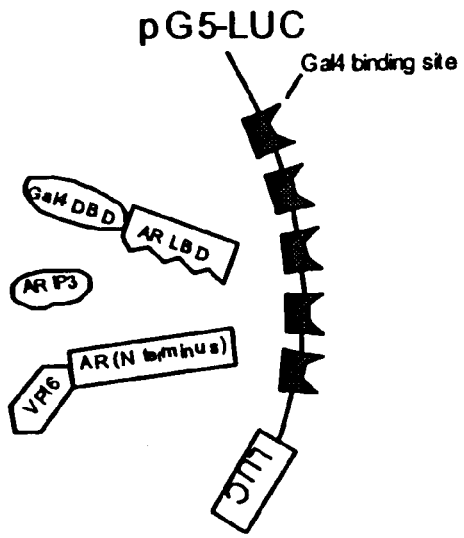
FIGS. 1A and 1B show the principle of the mammalian cell bioassay to measure quantitating androgen bioactivity in human serum. Ligand-binding domain (LBD) and N-terminal region of androgen receptor (AR) were fused to Gal4 DNA-binding domain of Saccharomyces cerevisiae, and transcriptional activation domain protein VP16 of herpes simplex virus, respectively. COS-1 cells were cotransfected with the plasmids encoding the latter fusion proteins, AR-interacting protein 3 (ARIP3), and luciferase (pG5-LUC) (FIG. 1A). Androgen binding (FIG. 1B) results in interaction between LBD and N-terminal region and of AR, which is enhanced by ARIP3. VP16 activation domains become tethered to the regulatory region of the luciferase gene, which leads to activation of luciferase gene transcription.

The assay according to the present invention has appeared useful for quantitation of circulating androgen bioactivity in human serum, also in pediatric patients. Thus we expect that the assay will have wide ramifications in clinical endocrinology.

According to another embodiment, we believe that the assay according to the present invention is very useful for screening test compounds with respect to their androgenic activity. In this case, instead of a serum sample, a solution of the test compound is contacted with the transfected cell.

According to a further embodiment, this method is also applicable for measuring anti-androgenic activity of a test compound in solution, or a serum sample. In this ease, the luciferase activity emitted from a first sample comprising a first compound having androgenie activity is measured. Next, the luciferase activity emitted from a second sample comprising said first compound having androgenic activity and either I) a second compound which shall be tested in respect of anti-androgenic activity, or II) serum is measured. The luciferase activities obtained from the two measurements are compared and the decreased luciferase activity emitted from said second sample is used to detect or quantify the anti-androgenic activity of the second compound or serum.

In case the androgenic activity of a serum sample shall be studied, it is preferably to treat the sample in order to release the androgen from binding proteins before the sample is contacted with the cell. Such treatment can, for example, be extraction with diethylether.

The cell to be transfected shall be a cell which is not androgen sensitive. Suitable cells are mammalian cells although the invention is not restricted hereto. For example, yeast cells fulfilling this condition may also be employed. A suitable mammalian cell is the COS-1 cell (ATCC No. CRL1650).

According to a preferable embodiment, the the luciferase reporter plasmid is pG5-LUC, the vector cloned with the ligand-binding domain of the human androgen receptor is pM-hAR, comprising the amino acids 657–919, the vector cloned with the N-terminal region of the rat androgen receptor is pVP16-rAR, comprising the amino acids 5–538, and the vector cloned with the androgen receptor-interacting protein 3 is pFLAG-ARIP3.

The bioassay according to the present invention, based on ARIP3-facilitated interaction between the LBD and N-terminal region of AR, has many advantages over known methods. As the assay is based on the use of a transfected cell, the preparation of the probe can be carried out just by cultivating the cell. The assay is very sensitive and specific. It has a wide dynamic range, and exhibits minimal cross reactivity to estradiol. For example, in boys, serum androgen bioactivity levels and testosterone concentrations measured by RIA correlated strongly, but bioactivity levels were lower, which probably reflects binding of androgens to SHBG.

The invention will be illuminated by the following non-restrictive Experimental Section.

EXPERIMENTAL SECTION

We have developed a mammalian cell (COS-1) bioassay, which can measure androgen bioactivity directly from a small amount (10 $\mu$l) of human serum. The recombinant assay is based on androgen-dependent interaction between the ligand-binding domain and the N-terminal region of androgen receptor (AR), which were fused to Gal4 DNA-binding domain of *Saccharomyces cerevisiae* and transcriptional activation domain of herpes simplex VP16 protein, respectively. The interaction is amplified by coexpressing AR-interacting protein 3 (ARIP3) in the cells. The reporter plasmid contained five Gal4 binding sites upstream of luciferase gene; luciferase activity in cell lysates is derived from androgen bioactivity in human serum. Saturating concentration of testosterone in fetal calf serum (FCS) induced>700-fold induction in relative luciferase activity. The sensitivity was<1.0 nmol/L of testosterone in FCS. The intra- and interassay coefficient of variations were 8.3% and 25%, respectively. Interaction between the AR termini was blocked by nonsteroidal antiandrogens, and the assay exhibited minimal cross-reactivity with estradiol. Serum androgen bioactivity was studied in 23 boys with constitutional delay of puberty (CDP; aged, 13.9 to 16.8 yrs), and in 9 prepubertal boys with cryptorchidism (aged, 1.0 to 6.4 yrs). Androgen bioactivity was detectable in 15 boys with CDP, and in all boys with cryptorchidism during treatment with hCG (range, 1.0–14.5 testosterone equivalents). Serum androgen bioactivity measured by the bioassay correlated strongly to serum testosterone concentration (r=0.93, P<0.0001, n=22), but not to dihydrotestosterone, DHEA, or androstenedione levels.

Materials and Methods

Plasmids. All plasmid constructs have been reported previously (4, 6–7), and only a short description of each is given here. The LBD of human AR (containing amino acids 657–919) (7), and the N-terminal region of rat AR(5–538) (4) were created by PCR and the products were cloned into the pM and VP16 vectors (CLONTECH Laboratories Inc., Palo Alto, Calif.), respectively. The luciferase reporter pG5-LUC contains five Gal4-binding sites in front of the minimal TATA box. pFLAG-ARIP3 has been described (6).

Cell culture and transfection. COS-1 cells (American Type Culture Collection) were maintained in phenol red-free Dulbecco's minimal essential medium (DMEM; Gibco BRL, Santa Clara, Calif.) containing penicillin (25 units/ml), streptomycin (25 units/ml), and 10% (vol/vol) fetal calf serum (FCS; Gibco BRL, Paisley, UK). Twenty-four hours before transfection, the cells were divided onto a 96-well plate (NUNC, Roskilde, Denmark) at a density of 1000 cells/well. The plates were incubated overnight at 37° C. in a humidified athmosphere of 5% $CO_2$/air. Three hours before transfection, the cell culture medium was replaced by DMEM containing 8% of charcoal-stripped FCS. The cells were transfected using FuGene reagent (Roche Molecular Biochemicals, Mannheim, Germany) according to the instructions provided by the manufacturer. Each well received a total of 49 ng DNA (pG5-LUC, 18 ng; pM-hAR (657–919), 9 ng; pFLAG-ARIP3, 9 ng; pVP16-rAR(5–538), 9 ng; and pCMVβ4 ng).

Twenty-four hours after transfection, medium in each well was replaced by 90 μl of phenol red-free DMEM without FCS, and 10 μl of testosterone-containing FCS in triplicate (standard) or 10 μl human serum (unknown sample) in duplicate was added. After an overnight incubation at 37° C. humidified atmosphere of 5% $CO_2$/air, the wells were aspirated empty, the cells were lysed in 30 μl of diluted reporter lysis buffer (Promega, Madison, Wis.), and 10 μl of cell lysates were transferred to 96-well plates for measurements of β-galactosidase (8) and luciferase (9) activities.

Sex steroids and nonsteroidal antiandrogens. Dehydroepiandrosterone (DHEA; 3β-hydroxy-5-androsten-17-one), androstenedione (4-androstene-3,17-dione), and 5α-dihydrotestosterone (DHT; 17β-hydroxy-5α-androstan-3-one), obtained from Steraloids Inc. (Wilton, N.H.), were dissolved and serially diluted in ethanol, and added to charcoal-stripped FCS to yield the following concentrations: 6.13 nmol/L, 25 nmol/L, and 100 nmol/L. DHT was diluted further in FCS to result a serum concentration of 0.78 nmol/L. These steroids were tested in the bioassay in parallel with testosterone standard curve. To investigate the transactivation potential of estradiol, 17β-estradiol was dissolved in charcoal-stripped FCS to result serum concentration of 500 nmol/L. The nonsteroidal antiandrogens Casodex ((2RS)-4'-cyano-3-(4-fluorophenylsulfony)-2-hydroxy-2-methyl-3'(trifluoromethyl-propionanilide), and hydroxyflutamide (4-hydroxy-α,α,α-trifluoro-2-methyl-4'-nitro-m-propionotoluidide) were obtained from Zeneca Pharmaceuticals (Macclesfield, UK) and Schering Corp. (Bloomfeld, N.J.), respectively. Antiandrogens were serially dissolved in ethanol, and added to charcoal-stripped FCS containing 10 nmol/L of testosterone. The highest antiandrogen concentrations in the resulting FCS were 1 μmol/L of hydroxyflutamide and 10 μmol/L of Casodex; the measurements were carried out in quadruplicate in one transfection.

Preparation of standards and patient sera for the bioassay. Testosterone (Steraloids Inc., Wilton, N.H.) was dissolved, serially diluted in ethanol, added to charcoal-stripped fetal calf serum (FCS; HyClone, Logan, Utah), and divided in aliquots, which were stored at −70° C. for future use as standards in the bioassay. Sixty microliters of serum from each boy (see below) was centrifuged briefly, filtered through a 0.22 μm Spin-X centrifuge filter unit (Corning Costar Corporation, New York, N.Y.), and stored at −70° C. until used.

Ether extraction. Testosterone was added to pooled serum of 10 prepubertal (age range, 1.0–8.0 yr) boys with cryptorchidism (13). The serum pool was divided in 300 μl aliquots in glass tubes, followed by 300 μl of diethylether (Merck, Darmstadt, Germany). The tubes were vortexed briefly, centrifuged for 10 minutes in 4° C., and placed in dry ice-ethanol (−70° C.) bath to freeze the water phase, after which the organic phase was transferred to a new glass tube. Freezing was repeated once, diethylether was evaporated, and the samples were reconstituted in 300 μl of charcoal-stripped FCS (5 tubes). The tubes were shaken gently overnight in 4° C., and filtered through a 0.22 μm Spin-X centrifuge filter unit. 30–60 μl of serum from each tube was taken for testosterone RIA (see below). Serum sex hormone-binding globulin (SHBG) level in the pooled sera of the boys (and in charcoal stripped FCS) was measured using the assay described below.

Subjects. Thirty-two boys, aged 1.0–16.8 yr, were investigated. Twenty-three boys, aged 13.9–16.8 yr, had constitutional delay of puberty (CDP). Clinical data, together with serum hormone levels on 19 boys have been published previously (10). The boys were in early puberty (18 boys were at Tanner stage G2, and 5 at stage G3), and had no underlying diseases that could have accounted for the delay in puberty. Sixty-five per cent had a history of pubertal delay in the family. The boys were clinically examined, puberty was staged according to Tanner (11), the testes were measured with a ruler, testicular volume was calculated from the formula length×width$^2$×0.52 (12), and a single blood sample was drawn. Twenty-two boys have been followed up≧12 months; puberty has progressed in each subject. Another study group consisted of nine boys aged 1.0–6.4 yr with cryptorchidism (clinical data and serum hormone levels have been published previously; 13). These boys were treated with human chorionic gonadotropin (hCG; 1500–5000 IU i.m., three times with one week interval). Blood samples were drawn immediately before the treatment and on the fourth day after the last hCG injection. The blood samples were allowed to clot, serum was separated by centrifugation and stored at −70° C. until required. The study protocol was accepted by the ethical committee of the Hospital for Children and Adolescents, University of Helsinki. Informed consents were obtained from the guardian, and in addition from the boys with CDP.

Immunoassays. Serum testosterone concentrations were measured using a commercially available RIA kit (Orion Diagnostica, Espoo, Finland; 10,13). According to the manufacturer, the assay has a 4.5% cross-reactivity with 5α-dihydrotestosterone, and minimal cross reactions to other steroid hormones. Serum DHT, androstenedione, and DHEA concentrations were measured in boys with CDP after separation of steroid fractions on Lipidex-5000 microcolumn (Packard-Becker, Groninger, The Netherlands) as previously described (14). Serum SHBG concentrations in twenty-two boys with CDP were measured using time-resolved fluoroimmunoassay (Wallac Oy, Turku, Finland). According to the manufacturer, the sensitivity of the SHBG assay is better than 0.5 nmol/L, inter- and intraassay coefficients of variation are both<5%. Data analysis. Relative luciferase activities were calculated by dividing luciferase acitivities by β-galactosidase activities to correct for differences in transfection efficiency. Standard curves for the bioassay were fitted with a 4 parameter weighted equation using the AssayZap program (Biosoft Inc., Cambridge, UK); the results are expressed in nmol/L testosterone equivalents. Pearson's correlation coefficient was calculated between paired variables to investigate their relationship. Mean values of different parameters were tested by paired and unpaired t tests, when appropriate. All mean values are expressed±SD. Statistical significance was accepted for $P<0.05$.

Results

Figure 1B:
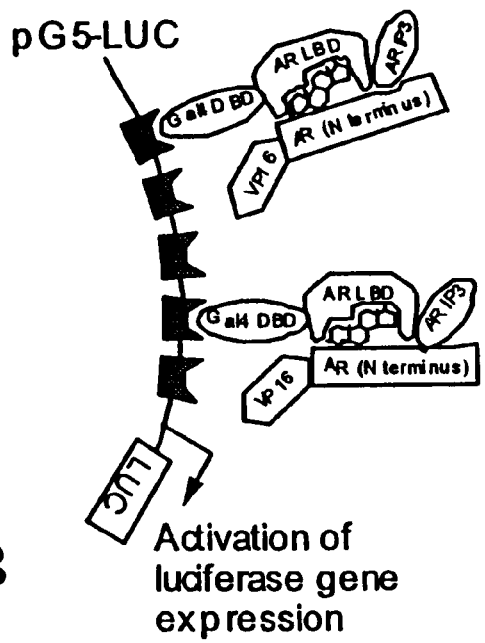

The principle of the bioassay for quantitating the response of mammalian cells to androgens in human serum is presented in FIG. 1. Androgens from the serum enter COS-1 cells and induce the interaction between the LBD and N-terminal region of AR. This interaction is enhanced by ARIP3 (6). The complexes bind to Gal4 binding sites, located in pG5-LUC and the VP16 transcriptional activation domains are tethered to the luciferase gene promoter, leading to activation of luciferase gene transcription. Luciferase activity in cell lysates corresponds to androgen bioactivity in human serum.

Figure 2:
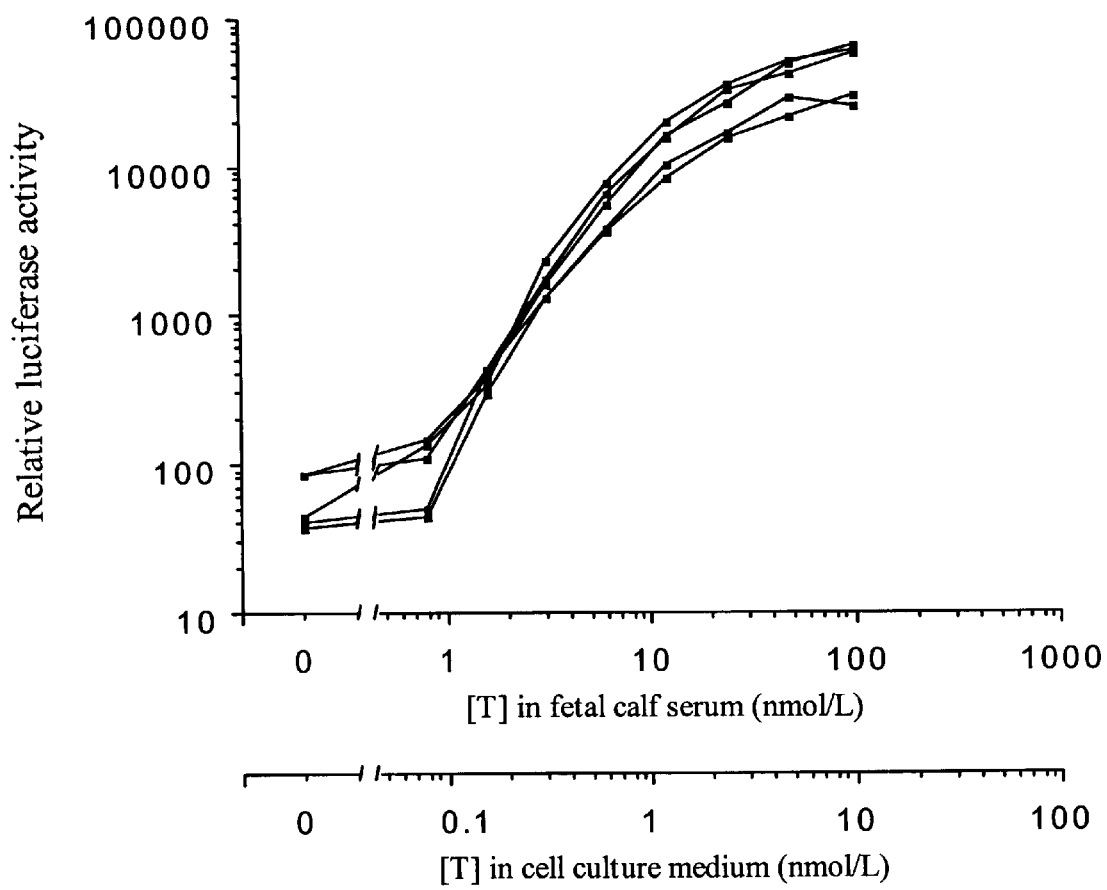
FIG. 2 shows dose response curves. Testosterone was added to charcoal-stripped fetal calf serum (upper x-axis); 10 µl of sera were added to 90 µl of cell culture medium. The resulting testosterone concentrations [T] in cell culture medium are shown on lower x-axis, and the resulting relative luciferase activities on y-axis. Relative luciferase activity refers to luciferase activities divided by β-galactosidase activities (β-galactosidase was used as an internal control for transfection efficiency). The curves are from 5 independent transfections, and each point represents the mean of 3 replicates.

Dose response. Different amounts of testosterone were added to charcoal-stripped FCS, and the resulting dose response curves are shown in FIG. 2. Values are presented as units of relative luciferase activity (luciferase activities divided by β-galactosidase activities obtained for each well). The steepest increase in relative luciferase activity occurred at testosterone concentrations in FCS below 10 nmol/L. The median of maximal fold induction (calculated as the ratio of relative luciferase activity induced by 100 nmol/L testosterone to activity induced by charcoal-stripped FCS without added testosterone) from 5 different assay runs was 745.

Biopotency of androgens and estrogen. To investigate the biopotencics of different naturally occurring androgens, DHT, androstenedione, and DHEA were added to charcoal-stripped FCS. Dihydrotestosterone was the most active androgen; FCS containing 0.78 nmol/L of DHT induced relative luciferase activity equal to 10.0 nmol/L testosterone equivalents. Only the highest concentration of androstenedione (100 nmol/L in FCS) induced a signal equal to 1.3 nmol/L of testosterone equivalents. DHEA did not activate luciferase gene expression at any dose. The relative luciferase activity induced by FCS containing a high concentration of estradiol (500 nmol/L) was<0.1% of that achieved with FCS containing saturating testosterone concentration (100 nmol/L).

Inhibition by nonsteroidal antiandrogens. The effect of antiandrogens on the interaction between the fragments of AR was investigated by first adding testosterone to charcoal stripped FCS to yield a subsaturating concentration (10 nmol/L). Then, increasing amounts of hydroxyflutamide and Casodex were added to aliquots of the testosterone-containing FCS, and 10 µl of each dilution was subjected to measurement in the bioassay. FCS containing 100 (hydroxyflutamide) or 1000 (Casodex) (i.e. clinically achievable concentrations of antiandrogens) times the molar amount of testosterone, suppressed relative luciferase activities to a level corresponding ~5% of the activity achieved by testosterone-containing FCS without added antiandrogens.

Sensitivity and precision. The sensitivity of the bioassay was defined as mean+2 standard deviations of multiple luciferase activities induced by charcoal-stripped FCS without added testosterone; it was below the signal induced by FCS containing 1.0 nmol/L of testosterone (cell culture medium containing 0.1 nmol/L of testosterone). Intraassay coefficient of variation (CV) was defined as repeated measurement of the same human serum sample. At 4.9 nmol/L testosterone equivalents, the intraassay CV was 8.3%. Interassay CV was 25% (as determined from 5 assay runs).

Figure 3:
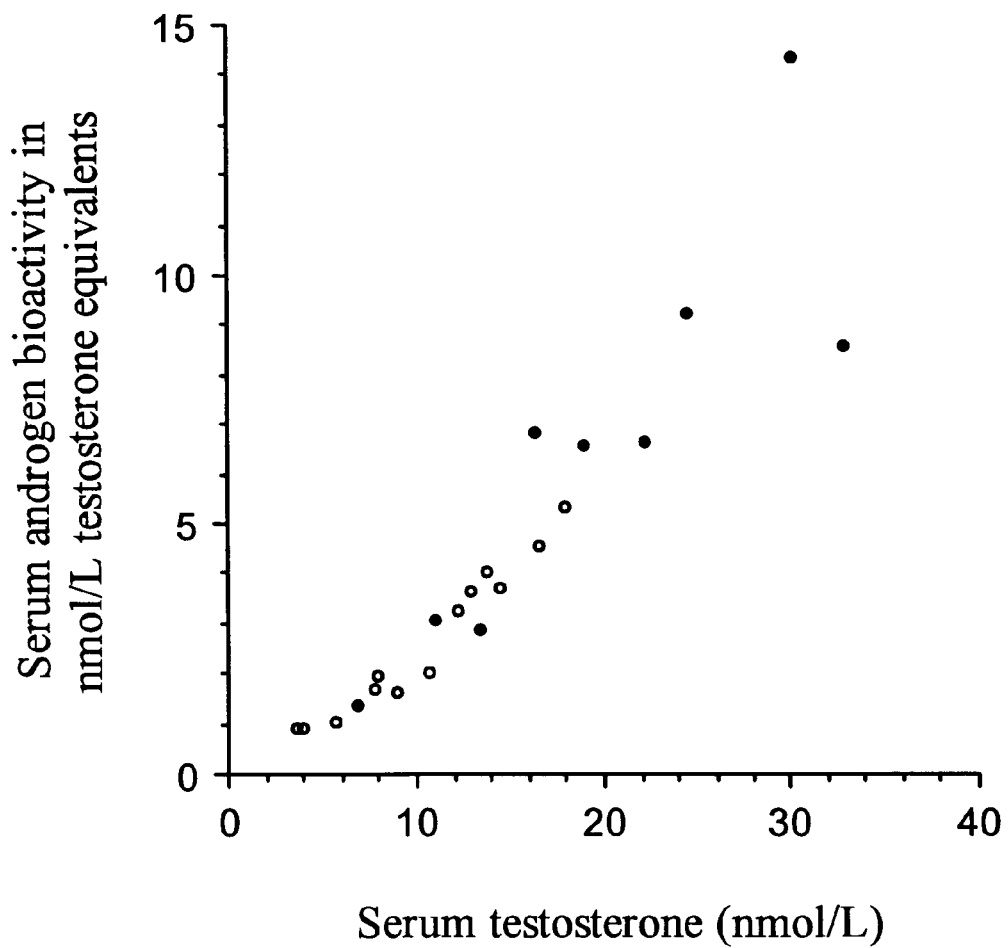
FIG. 3 shows serum testosterone concentration by RIA (x-axis), against serum androgen bioactivity in nmol/L testosterone equivalents (y-axis) by the mammalian cell bioassay. Open circles, boys with constitutional delay of puberty (n=13). Closed circles, prepubertal boys with cryptorchidism (n=9) during hCG treatment.

Patient data. Serum androgen bioactivity levels were above the assay sensitivity in 15 boys with CDP, and in all 9 prepubertal boys with cryptorchidism during treatment with hCG (androgen bioactivity levels before the hCG treatment were below the detection limit of the assay). The mean of androgen bioactivity levels above the assay sensitivity was 4.3±3.2 nmol/L, and range 1.0–14.5 nmol/L testosterone equivalents (n=24). These values were on the rising part of the dose response curve, and correlated strongly to serum testosterone levels measured by RIA (r=0.93, P<0.0001, n=22; FIG. 3). When expressed as a function of serum total testosterone, the average serum androgen bioactivity levels were 26±3.7% and 33±9% in boys with CDP or cryptorchidism, respectively (P<0.05). In boys with CDP, this percentage and testis volume correlated positively (r=0.49, n=13, P=0.09).

In boys with CDP, serum androgen bioactivity levels did not correlate to serum DHEA (range, 4.7–21.1 nmol/L), DHT (0.3–3.4 nmol/L), or androstenedione (0.9–4.4 nmol/L) concentrations. When investigating the relationship between bioactivity levels and SHBG, relative luciferase activities below the sensitivity of the bioassay were set equal to the detection limit of the bioassay. One boy had clearly higher serum SHBG level (250 nmol/L) than the others with CDP (range, 36–125 nmol/L), and this value was excluded from all correlation analyses. Androgen bioactivity levels correlated negatively to serum SHBG concentrations (r=0.44, P<0.05, n=21), and positively to testicular volumes (r=0.77, P<0.0001, n=23)

Figure 4:
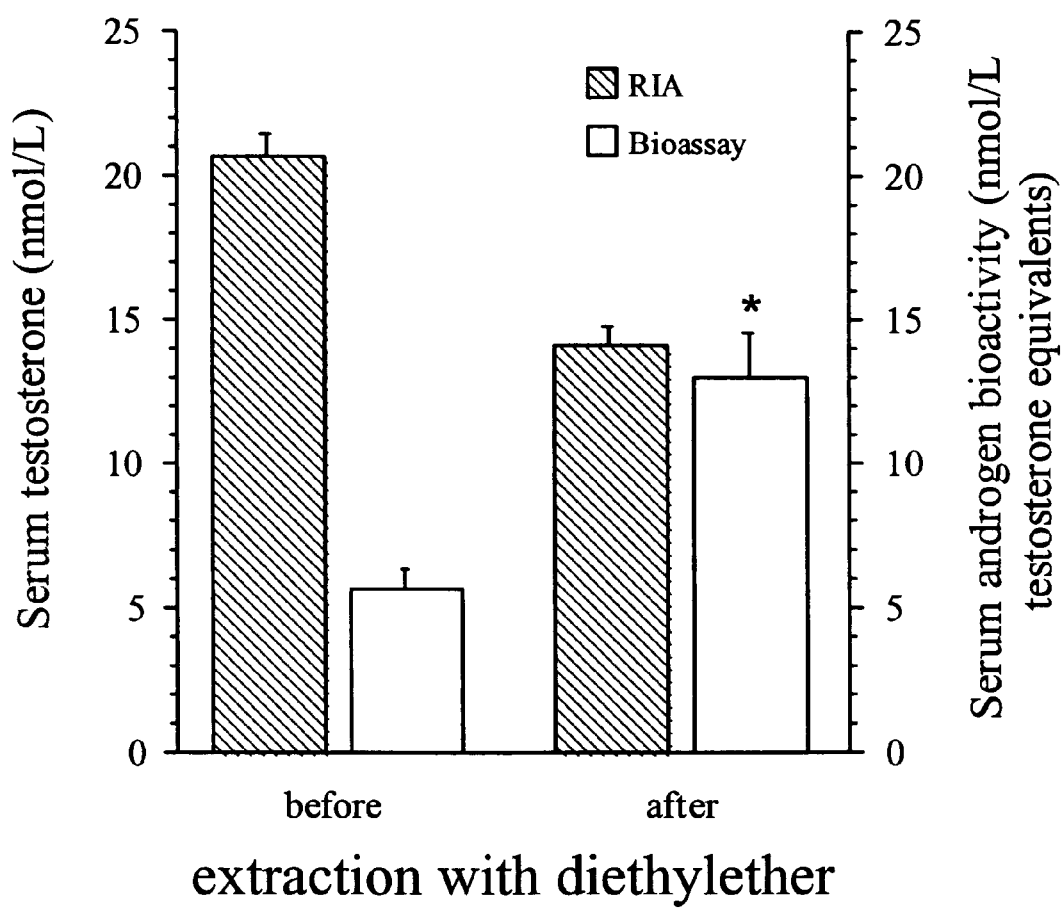
FIG. 4 shows testosterone and androgen bioactivity levels in human serum pool after adding of testosterone. Sera of 10 prepubertal boys with cryptorchidism were pooled, testosterone was added to yield concentration of 21 nmol/L, and testosterone (RIA, hatced bars) and androgen bioactivity levels (mammalian cell bioassay, open bars) were measured. To release testosterone from the binding proteins, serum was extracted with diethylether, the steroid-containing phase was reconstituted in charcoal stripped FCS, and the measurements were repeated. Asterisk, different from the mean androgen bioactivity level before extraction-reconstitution procedure (P<0.005). Each bar represents mean+SD of 5 measurements.

Ether extraction of human serum. To investigate the relationship between serum androgen bioactivity and testosterone levels further, testosterone was added to pooled sera of 10 prepubertal boys with cryptorchidism to yield serum concentration of 21 nmol/L. In this pool, serum testosterone concentration, measured with RIA, was 20.6±0.9 nmol/L, and androgen bioactivity level, measured with the bioassay, was 5.7±0.6 nmol/L testosterone equivalents (FIG. 4). Concentration of SHBG in this serum pool was 135 nmol/L. We next extracted the pooled sera with diethylether, which releases steroid hormones from their binding proteins; the steroid-containing phase was reconstituted in charcoal stripped FCS (without measurable SHBG). This should render free plus initially protein-bound androgens in human serum available to the cells of the bioassay. Indeed, after the procedure, serum androgen bioactivity in the pool increased from 5.7±0.6 nmol/L to 13.0±1.6 nmol/L testosterone equivalents (FIG. 4; P<0.005). The actual rise in serum androgen bioactivity was likely to be even higher, as not all testosterone was recovered even by the RIA; the mean testosterone level measured after reconstitution was 14.1±1.3 nmol/L (mean recovery 69%; FIG. 4).

Discussion

The earliest assays for measuring bioactivity of androgenic compounds were based on androgen-dependent responses of living organisms, like the growth of the capon comb or accessory sex organs of the male rat (15). Development of cell culture and recombinant DNA techniques have enabled more sensitive and precise assays for evaluating biological responses of living cells to sex steroids. Nevertheless, the only assay so far that measures sex steroid bioactivity in human serum has been the recombinant ultrasensitive bioassay for estrogens, which utilizes yeast cells (16). Yeast cells were not suitable for the current bioassay since, probably due to permeability properties of the cell wall, nonsteroidal antiandrogens did not show any antagonistic activity in yeast cells (7). To our knowledge the current mammalian cell assay, based on ARIP3-enhanced interaction between the fragments of AR, is the first to measure androgen bioactivity in human serum.

The sensitivity of the assay was better than the signal induced by 1.0 nmol/L of testosterone in the 10 µl FCS aliquot, corresponding to 0.1 nmol/L of testosterone in cell culture medium. This is of the same order of magnitude as the $K_D$ of AR for testosterone (17,18), which casts some doubt on the possibility to enhance the assay sensitivity without additional manipulation of the sample significantly. Although ether extraction and subsequent concentration of the sample in FCS increased the relative sensitivity of the bioassay, the assay without the extraction procedure has the benefit of directly measuring androgen bioactivity in human serum.

In boys, serum androgen bioactivity and testosterone concentrations correlated strongly. Testosterone in serum is bound with high affinity to SHBG and with low affinity to albumin; only ~2–3% of total testosterone is free (18,19). The amount of biologically active testosterone has been suggested to be a function of free testosterone (20). The androgen bioactivity levels we found, however, were obviously too high to represent merely the free testosterone fraction (21). Indeed, in the course of the assay, sera were diluted to cell culture medium in a ratio of 1 to 10, which should lead to dissociation of the weakest protein-steroid complexes. Thereafter, both the free plus initially albumin bound testosterone fractions in serum, which together are often referred to as the bioavailable testosterone (20, 23–25), should be available for the cells of the bioassay.

On the other hand, because of the high androgenic potential of DHT in FCS, one would expect to find a positive correlation between serum androgen bioactivity and DHT levels in boys with CDP. Lack of relationship between these variables may, however, reflect the fact that the affinity of DHT to SHBG is three times that of testosterone (26), which may render the low amounts of circulating DHT in boys biologically inert. Moreover, adding of testosterone to SHBG-containing serum pool of prepubertal boys, resulted to androgen bioactivity levels which were approximately one fourth of the testosterone levels measured with RIA. In similar vein, extraction of human serum with diethylether and subsequent reconstitution of the sample to charcoal-stripped FCS increased bioactivity levels. Taken together, although we can not exclude the existence of yet unidentified factor(s) in human serum that inhibit sex steroid entry or action within the target cells, these findings suggest that SHBG-bound steroids are not available to COS-1 cells of the bioassay.

Serum androgen bioactivity levels and testis volumes correlated strongly, which probably reflects increased testicular testosterone production towards adulthood. The ratio of serum androgen bioactivity to testosterone also tended to increase as a function of puberty, which would be expected, because of the reciprocal changes in serum testosterone and SHBG levels during adolescence (27,28). On the other hand, this ratio was higher in prepubertal boys with cryptorchidism during hCG treatment than in the older boys with CDP. This was not expected, because prepubertal subjects have higher serum SHBG levels (27) than boys in early puberty.

The androgen-dependent interaction between the fragments of AR exhibits minimal cross reactivity to estradiol (3,5). This was also observed in the present study. Moreover, nonsteroidal antiandrogens Casodex and hydroxyflutamide suppressed relative luciferase activity, suggesting that the current assay is applicable to screen rapidly compounds for both androgenic and antiandrogenic activity. However, caution is required in the interpretation of these results, since in the assays employing fragments of AR or full-length AR, some synthetic compounds may act differently (5). Nevertheless, our unpublished results indicate that androgen bioactivity levels in boys measured with the current assay correlate strongly with those measured by an assay based on the use of full-length AR.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

REFERENCES

1. Mangelsdorf D J, Evans R M. 1995 The RXR heterodimers and orphan receptors. Cell. 83: 841–850.
2. Langley E Z, Zhou X, Wilson E M. 1995 Evidence for an anti-parallel orientation of the ligand-activated human androgen receptor dimer. J Biol Chem. 270: 29983–29990.
3. Doesburg P, Kuil C W, Berrevoets C A, et al. 1997 Functional in vivo interaction between the amino-terminal, transactivation domain and the ligand-binding domain of the androgen receptor. Biochemistry. 36: 1052–64.
4. Ikonen T, Palvimo J J, Jänne O A. 1997 Interaction between the amino- and carboxyl-terminal regions of the rat androgen receptor modulates transcriptional activity and is influenced by nuclear receptor coactivators. J Biol Chem. 272: 29821–29828.
5. Kemppainen J A, Langley E, Wong C I, Bobseine K, Kelce W R, Wilson EM. 1999 Distinguishing androgen receptor agonists and antagonists: distinct mechanisms of activation by medroxyprogesterone acetate and dihydrotestosterone. Mol Endocrinol. 13: 440–454.
6. Moilanen A M, Karvonen U, Poukka H, et al. 1999 A testis-specific androgen receptor coregulator that belongs to a novel family of nuclear proteins. J Biol Chem. 274:3700–3704.
7. Moilanen A, Rouleau N, Ikonen T, Palvimo J J, Jänne O A. 1998 The presence of a transcription activation function in the hormone-binding domain of androgen receptor is revealed by studies in yeast cells. FEBS Lett. 412: 355–358.
8. Rosenthal N. 1987 Identification of regulatory elements of cloned genes with functional assays. Methods Enzymol. 152:704–720.
9. Palvimo J J, Partanen M, Jänne O A. 1996 Characterization of cell-specific modulatory element in the murine ornithine decarboxylase promoter. Biochem J. 316:993–998.
10. Raivio T, Saukkonen S, Jääskeläinen J, Komulainen J, Dunkel L. 2000 Signaling between the pituitary gland and the testes: inverse relationship between serum follicle-stimulating hormone and inhibin B concentrations in boys in early puberty. Eur J Endocrinol. 142:150–156.
11. Tanner J M. 1962 Growth at adolescence. $2^{nd}$ ed. Oxford, Blackwell Scientific Publications.
12. Hansen P, With T K. 1952 Clinical measurments of the testis in boys and men. Acta Med Scand 142 (Suppl 266):457–465.
13. Raivio T, Dunkel L. 1999 Inverse relationship between serum inhibin B and FSH levels in prepubertal boys with cryptorchidism. Pediatr Res. 46:496–500.
14. Apter D, Jänne O, Karvonen P, Vihko R. 1976 Simultaneous determination of five sex hormones in human serum by radioimmunoassay after chromatography on Lipidex-5000. Clin Chem. 22:32–38.
15. Dorfman R I. 1962 Androgens and anabolic agents. In: Dorfman R I (ed) Methods in Hormone Research, Volume II. New York, Academic Press; 275–313.
16. Klein K O, Baron J, Colli M J, McDonnell D P, Cutler G B. 1994 Estrogen levels in childhood determined by an ultrasensitive recombinant cell bioassay. J Clin Invest. 94: 2475–2480.
17. Sheridan P J. 1983 Androgen receptors in the brain: what are we measuring? Endocr Rev. 4:171–178.
18. Pardridge W M. 1988 Selective delivery of sex steroid hormones to tissues In vivo bu albumin and by sex hormone-binding globulin. Ann N Y Acad Sci 538: 173–192.
19. Vermeulen A. 1977 Transport and distribution of androgens at different ages. In: Martini L, Motta M (eds) Androgens and antiandrogens. New York, Raven Press; 53–65.
20. Siiteri P K, Murai J T, Hammond G L, Nisker J A, Raymoure W J, Kuhn R W. 1982 The serum transport of steroid hormones. Recent Prog Horm Res. 38:457–510.

21. Mendel C M. 1989 The free hormone hypothesis: a physiologically based mathematical model. Endocr Rev. 10:232–274.
22. Vermeulen A, Verdonck L, Kaufman J M. 1999 A critical evaluation of simple methods for the estimation of free testosterone in serum. J Clin Endocrinol Metab. 84:3666–3672.
23. Belgorosky A, Rivarola M A. 1987 Progressive increase in non-sex-hormone-binding globulin-bound testosterone from infancy to late prepuberty in boys. J Clin Endocrinol Metab. 64:482–485.
24. Morley J E, Kaiser F, Raum W J, et al. 1997 Potentially predictive and manipulable blood serum correlates of aging in the healthy human male: progressive decreases in bioavailable testosterone, dehydroepiandrosterone sulfate, and the ratio of insulin-like growth factor 1 to growth hormone. Proc Natl Acad Sci. 94:7537–7542.
25. Barrett-Connor E, Goodman-Gruen D, Patay B. 1999 Endogenous sex hormones and cognitive function in older men. J Clin Endocrinol Metab. 84:3681–3685.
26. Forest M G, Saez J M, Bertrand J. 1993 Biochemistry and physioloy of gonadotropic and gonadal hormones. In: Bertrand J, Rappaport R, Sizonenko P(eds) Pediatric endocrinology. Baltimore, Williams & Wilkins; 351–371.
27. Belgorosky A, Rivarola M A. 1987 Changes in serum sex hormone-binding globulin and in serum non-sex hormone binding globulin-bound testosterone during prepuberty in boys. J Steroid Biochem. 27:291–295.
28. Ducharme J R, Forest M G. Normal pubertal development. In; Bertrand J, Rappaport R, Sizonenko PC (eds) Pediatric Endocrinology. Baltimore, Williams & Wilkins; 373–386.

What is claimed is:

1. A method for determining the androgenic activity of a sample, comprising the steps of
    a) contacting the sample with a cell comprising
        a luciferase reporter plasmid,
        a fusion protein comprising a ligand-binding domain of the androgen receptor and
        a Gal4 DNA-binding domain, said fusion protein being able to bind to binding sites in said luciferase reporter plasmid,
        a fusion protein comprising an N-terminal region of the androgen receptor and a transcriptional activation domain, and
        an androgen receptor-interacting protein 3,
    b) allowing the sample to incubate with said cell,
    c) lysing said cell,
    d) measuring the luciferase activity of the lysate,
    e) comparing the measured luciferase activity to that obtained by repeating the steps a) to d) above except that a control is added instead of the sample, to give the relative luciferase activity of the sample, and
    f) using the relative luciferase activity to detect or quantify an active androgen in the sample.

2. The method according to claim 1 wherein the sample is a mammalian serum sample.

3. The method according to claim 2 wherein the serum sample is treated so as to release androgens from binding proteins before contacting the sample with the cell.

4. The method according to claim 1 wherein the sample is a solution comprising a compound to be tested in respect of its androgenic activity.

5. A method for determining the anti-androgenic activity of a compound, comprising the steps of
    a) measuring the luciferase activity emitted from a first sample comprising a first compound having androgenic activity, according to claim 4,
    b) measuring the luciferase activity, according to the previous step, emitted from a second sample comprising said first compound having androgenic activity and either I) a second compound which shall be tested in respect of anti-androgenic activity, or II) mammalian serum,
    c) comparing the luciferase activities obtained in steps a) and b) above, and
    d) using a decreased luciferase activity emitted from said second sample to detect or quantify the anti-androgenic activity of said second compound or serum.

6. The method according to any of the foregoing claims wherein the cell has been made by transfecting with
    the luciferase reporter plasmid pG5-LUC,
    a plasmid comprising a vector cloned with the ligand-binding domain of the human androgen receptor and a Gal4 DNA-binding domain, said plasmid being pM-hAR,
    comprising the amino acids 657–919 of human AR,
    a plasmid comprising a vector cloned with the N-terminal region of the rat androgen
    receptor and a transcriptional activation domain, said plasmid being pVP16-rAR, comprising the amino acids 5–538 of rat AR, and
    a plasmid comprising a vector cloned with the androgen receptor-interacting protein 3, said plasmid being pFLAG-ARIP3.

7. The method according to claim 6 wherein the cell is a mammalian cell.

8. The method according to claim 7 wherein the mammalian cell is COS-1.

9. A cell comprising
    a luciferase reporter plasmid,
    a fusion protein comprising the ligand-binding domain of the androgen receptor and
    a Gal4 DNA-binding domain, said fusion protein being able to bind to binding sites in said luciferase reporter plasmid
    a fusion protein comprising an N-terminal region of the androgen receptor and a transcriptional activation domain, and
    an androgen receptor-interacting protein 3.

10. The cell according to claim 9 wherein the cell has been made by transfecting with
    the luciferase reporter plasmid pG5-LUC,
    a plasmid comprising a vector cloned with the ligand-binding domain of the human androgen receptor and a Gal4 DNA-binding domain, said plasmid being pM-hAR,
    comprising the amino acids 657–919 of human AR,
    a plasmid comprising a vector cloned with the N-terminal region of the rat androgen receptor and a transcriptional activation domain, said plasmid being pVP16-rAR,
    comprising the amino acids 5–538 of rat AR, and
    a plasmid comprising a vector cloned with the androgen receptor-interacting protein 3, said plasmid being pFLAG-ARIP3.

11. The cell according to claim 10 wherein it is a mammalian cell.

12. The cell according to claim 11 wherein the mammalian is COS-1.

13. The method according to claim 1 wherein the sample is a human serum sample.

* * * * *